United States Patent [19]

Mishra et al.

[11] Patent Number: 4,845,236
[45] Date of Patent: Jul. 4, 1989

[54] 2-(TETRAHYDRO-2-THIENYL)PHENOLS AND CARBAMATE DERIVATIVES

[75] Inventors: Anupama Mishra, Guelph, Canada; Richard C. Moore, Wallingford, Conn.

[73] Assignees: Uniroyal Chemical Company, Inc., Middlebury, Conn.; Uniroyal Chemical Ltd./Ltee, Don Mills, Canada

[21] Appl. No.: 231,019

[22] Filed: Aug. 10, 1988

Related U.S. Application Data

[62] Division of Ser. No. 148,810, Jan. 27, 1988, Pat. No. 4,778,819.

[51] Int. Cl.[4] .............. C07D 333/12; C07D 333/22; C07D 409/00
[52] U.S. Cl. ...................... 549/75; 549/59; 549/77; 549/78
[58] Field of Search ............ 549/78, 75, 77, 59

[56] References Cited

U.S. PATENT DOCUMENTS

| | | | |
|---|---|---|---|
| 2,439,345 | 4/1948 | Morris | 549/78 |
| 4,757,084 | 7/1988 | Brftu | 549/78 |
| 4,778,819 | 10/1988 | Mishra et al. | 514/438 |

*Primary Examiner*—M. Alan Siegel
*Attorney, Agent, or Firm*—John A. Shedden

[57] ABSTRACT

A compound having the structural formula

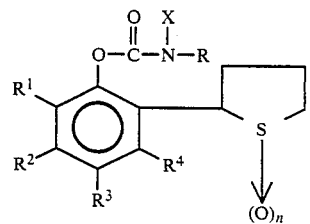

where R is $C_1$-$C_6$ alkyl or $C_5$-$C_6$ cycloalkyl;

X is hydrogen or methyl;

$R^1$, $R^2$, $R^3$ and $R^4$ are the same or different and are hydrogen, halogen, $C_1$-$C_8$ alkyl, $C_1$-$C_2$ haloalkyl, $C_3$-$C_6$ cycloalkyl, $C_7$-$C_9$ aralkyl, phenyl, nitro, $C_1$-$C_6$ alkoxy, $C_1$-$C_6$ alkylthio, $C_1$-$C_6$ alkylsulfinyl, $C_1$-$C_6$ alkylsulfonyl, $C_7$-$C_9$ aralkoxy, phenoxy, phenylthio, phenylsulfinyl, phenylsulfonyl, tetrahydro-2-thienyl, dioxytetrahydro-2-thienyl, alkali metal carboxylate, $C_2$-$C_5$ alkoxycarbonyl, phenoxycarbonyl or $N(R^5)R^6$;

$R^5$ and $R^6$ are the same or different and are hydrogen or $C_1$-$C_2$ alkyl; and n is 0, 1 or 2 is disclosed. A method for controlling insects using an insecticidally effective amount of this compound is also taught. In addition, an insecticidal composition comprising an insecticidally effective amount of the compound and a carrier therefor is provided.

3 Claims, No Drawings

2-(TETRAHYDRO-2-THIENYL)PHENOLS AND CARBAMATE DERIVATIVES

This is a division of application Ser. No. 148,810 filed Jan. 27, 1988 now U.S. Pat. 4,778,819.

BACKGROUND OF THE INVENTION

1. Field of the Invention

The instant invention is directed to a class of 2-(tetrahydro-2-thienyl)phenols and carbamate derivatives thereof. More specifically, the instant invention is directed to a class of 2-(tetrahydro-2-thienyl)phenols useful as intermediates in the production of carbamate derivatives of 2-(tetrahydro-2-thienyl) phenols useful as insecticides.

2. Background of the Prior Art

The devastations caused by insects represent a serious economic threat to commerically important food, fiber and ornamental plants. Particularly serious is the attacks of insects against such important grain plants as corn and rice. For this reason the development of new, more effective insecticides represents an ongoing scientific activity. It is particularly important to develop insecticides effective at very low dosages. Such insecticides combine the necessary control of insects without attendant enbironmental difficulties.

The chemistry of reacting substituted phenols is known in the art. Gassman et al., J. Am. Chem. Soc., 100, 7611 (1978) describes methods for the ortho-formylation of phenols. Although a plurality of compounds are synthesized in accordance with the methods disclosed therein no 2-(tetrahydro-2-thienyl)phenols, with the exception of 2-methyl-6-(tetrahydro-2-thienyl) phenol, are disclosed therein. No utility for this compound, or for any of the other compounds synthesized in Gassman et al., is disclosed.

The utilization of aromatic substituted methyl or higher alkyl carbamates having insecticidal properties is well known in the art. One of the earliest of such disclosures in U.S. Pat. No. 2,903,478 which describes 1-napthyl N-alkyl carbamates as having insecticidal properties against insect pests of fruits, vegetables, cotton and other plants.

U.S. Pat. Nos. 3,062,864, 3,062,865, 3,062,866, 3,062,867, and 3,062,868 disclose a group of N-methylcarbamates. The first four of these patents are N-methylcarbamates substituted with phenyl groups in which teh phenyl substituted rings are themselves substituted in the meta position with alkyls. The substituted alkyls of the first four recited patents are, respectively, 1-methylbutyl, m-sec. butyl, 1-methylhexyl and 1-ethylpropyl. Each of these compounds are recited to have insecticidal properties. The last patent of this group, U.S. Pat. No. 3,062,868, discloses 3-t-amyl-6-bromophenyl N-methylcarbamate, also claimed to possess insecticidal properties.

Additional N-methylcarbamates useful as insecticides are set forth in U.S. Pat. No. 3,111,539. This patent teaches o-(2-isopropoxyphenyl)-N-methylcarbamate as well as o-(2-isopropoxyphenyl)-N,N-dimethylcarbamate.

U.S. Pat. No. 3,167,472 describes the insecticidal use of 3-methyl-5-(1-methylethyl)phenol esters of N-monomethyl and N,N-dimethyl carbamic acid.

Yet another disclosure of a carbamic acid ester having insecticidal properties is the disclosure in U.S. Pat. No. 3,336,186 which describes N,N-dialkyl-N-(3-(alkylamino)carbonyl)oxylphenylalkanimides. These compounds are said, in the '186 patent, to possess pesticidal properties against mites.

Additional N-methylcarabamates having insecticidal properties includes 2-(1-methylpropyl)phenyl-N-methylcarbamate described by Metcalf et al., J. Econ. Entomol., 55, 889 (1962).

It is noted that all of the above phenyl N-substituted carbamates include no sulfur containing substituents. French Pat. No. 1,275,658 describes a nonsystemic insecticde which includes a sulfur-containing substituent on the phenyl substituent of the N-methyl carbamate. However, this is a multiple substituted phenyl group and the sulfur-containing compound is far removed from that of the present invention. German Offen. No. 1,910,588 describes 2-(ethylthiomethyl)phenyl-N-methylcarbamate as a systemic insecticide. This sulfur-containing compound is also far removed from the compounds of the present application.

Finally, U.S. Pat. No. 4,481,216 teaches control of corn rootworm by application of N-methyl 2-(1-methylethyl)phenylcarbamate.

Although the above references are directed to compounds used in the control of insects, there still is a continuing need for improved insecticides having specific application to commercially important plants but which can be utilized in very low dosage to minimize environmental side effects.

SUMMARY OF THE INVENTION

A new class of compounds have now been discovered which have particular application as insecticides, being particularly effective against insects which attack commercially important grain plants, but which can be applied in very low concentration.

In accordance with the instant invention a class of compounds having the structural formula

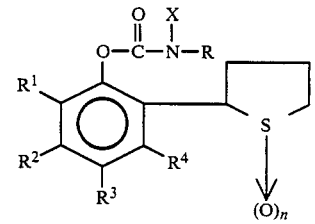

where R is $C_1$–$C_6$ alkyl or $C_5$–$C_6$ cycloalkyl;

X is hydrogen or $C_1$–$C_6$ alkyl;

$R^1$, $R^2$, $R^3$, and $R^4$ are the same or different and are hydrogen, halogen, $C_1$–$C_8$ alkyl, $C_1$–$C_2$ haloalkyl, $C_3$–$C_6$ cycloalkyl, $C_7$–$C_9$ aralkyl, phenyl, nitro, $C_1$–$C_6$ alkoxy, $C_1$–$C_6$ alkylthio, $C_1$–$C_6$ alkylsulfinyl, $C_1$–$C_6$ alkylsulfonyl, $C_7$–$C_9$ aralkoxy, phenoxy, phenylthio, phenylsulfinyl, phenylsulfonyl, tetrahydro-2-thienyl, dioxytetrahydro-2-thienyl, alkali metal carboxylate, $C_2$–$C_5$ alkoxycarbonyl, phenoxycarbonyl or $N(R^5)R^6$;

$R^5$ and $R^6$ are the same or different and are hydrogen or $C_1$–$C_2$ alkyl; and n is 0, 1 and 2.

In further accordance with the instant invention an insecticidal composition comprising the compound above and a carrier therefore is provided.

In still further accordance with the present invention a method for controlling insects comprising applying to the locus to be protected an insecticidally effective amount of the compound above is described.

In yet further accordance with the present invention a class of substituted phenol compounds having the structural formula

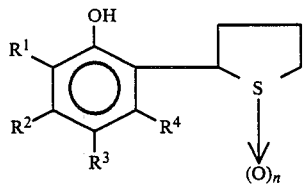

where $R^1$, $R^2$, $R^3$ and $R^4$ are the same or different and are hydrogen, halogen, $C_1$-$C_8$ alkyl, $C_1$-$C_2$ haloalkyl, $C_3$-$C_6$ cycloalkyl, $C_7$-$C_9$ aralkyl, phenyl, nitro, $C_1$-$C_6$ alkoxy, $C_1$-$C_6$ alkylthio, $C_1$-$C_6$ alkylsulfinyl, $C_1$-$C_6$ alkylsulfonyl, $C_7$-$C_9$ aralkoxy, phenoxy, phenylthio, phenylsulfinyl, phenylsulfonyl, tetrahydro-2-thienyl, dioxytetrahydro-2-thienyl, alkali metal carboxylate, $C_2$-$C_5$ alkoxycarbonyl, phenoxycarbonyl or $N(R^5)R^6$;

$R^5$ and $R^6$ are the same or different and are hydrogen or $C_1$-$C_2$ alkyl; and n is 0, 1 or 2;

with the proviso that when n is 0 and $R^2$, $R^3$, and $R^4$ are each hydrogen then $R^1$ cannot be methyl are set forth.

In yet still futher accordance with the present invention a process for making the compound having the formula

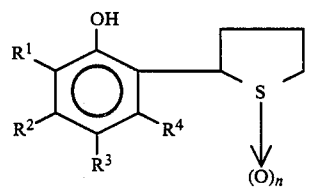

where $R^1$, $R^2$, $R^3$, $R^4$, $R^5$, $R^6$ and n have the meanings given for the compound discussed immediately above is provided. In this process a phenol or substituted phenol having the structural formula

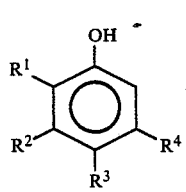

where $R^1$, $R^2$, $R^3$ and $R^4$ have the meanings given above for the product is reacted with tetrahydrothiophene in the presence of N-chlorosuccinimide and triethylamine.

Finally, in even still further accordance with the present invention a process for producing a compound having the structural formula

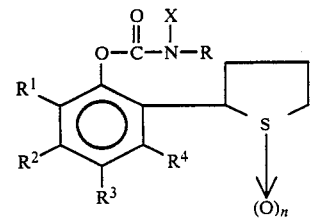

where R is $C_1$-$C_6$ alkyl or $C_5$-$C_6$ cycloalkyl;

X is hydrogen or $C_1$-$C_6$ alkyl;

$R^1$, $R^2$, $R^3$, $R^4$, are the same or different and are hydrogen, halogen, $C_1$-$C_8$ alkyl, $C_1$-$C_2$ haloalkyl, $C_3$-$C_6$ cycloalkyl, $C_7$-$C_9$ aralkyl, phenyl, nitro, $C_1$-$C_6$ alkoxy, $C_1$-$C_6$ alkylthio, $C_1$-$C_6$ alkylsulfinyl, $C_1$-$C_6$ alkylsulfonyl, $C_7$-$C_9$ aralkoxy, phenoxy, phenylthio, phenylsulfinyl, phenylsulfonyl, tetrahydro-2-thienyl, dioxytetrahydro-2-thenyl, alkali metal caraboxyalte, $C_2$-$C_5$ alkoxycarbonyl, phenoxycarbonyl or $NR^5R^6$;

$R^5$ and $R^6$ are the same or differenct and are hydrogen or $C_1$-$C_2$ alkyl; and n is 0, 1 and 2.

In this process, a substituted phenol having the structural formula

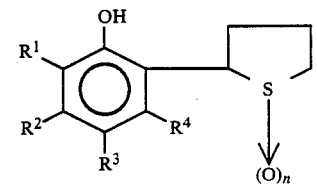

where $R^1$, $R^2$, $R^3$, $R^4$, and n have the meanings given for the product of this reaction is reacted with an alkylisocyanate in the presence of a catalytically effective amount of a catalyst selected from the group consisting of a dialkyl tin oxalate and a trialkylamine.

DETAILED DESCRIPTION

The carbamate derivatives of a class of substituted phenols of the present application has the structural formula

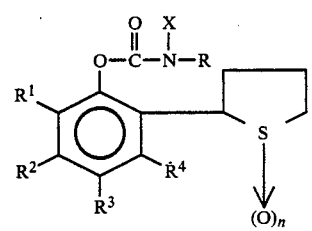

I where R is $C_1$-$C_6$ alkyl or $C_5$-$C_6$ cycloalkyl;

X is hydrogen or $C_1$-$C_6$ alkyl;

$R^1$, $R^2$, $R^3$, $R^4$ are the same or different and are hydrogen, halogen, $C_1$-$C_8$ alkyl, $C_1$-$C_2$ haloalkyl, $C_3$-$C_6$ cycloalkyl, $C_7$-$C_9$ aralkyl, phenyl, nitro, $C_1$-$C_6$ alkoxy, $C_1$-$C_6$ alkylthio, $C_1$-$C_6$ alkylsulfinyl, $C_1$-$C_6$ alkylsulfonyl, $C_7$-$C_9$ aralkoxy, phenoxy, phenylthio, phenylsulfinyl, phenylsulfonyl, tetrahydro-2-thienyl, dioxytetrahydro-2-thienyl, alkali metal carboxylate, $C_2$-$C_5$ alkoxycarbonyl, phenoxycarbonyl or $N(R^5)R^6$;

$R^5$ and $R^6$ are the same or different and are hydrogen or $C_1-C_2$ alkyl; and n is 0, 1 and 2.

More preferably, the compound of the present invention has the structural formula (I) where R is methyl, isopropyl or cyclohexyl;

X is hydrogen or methyl; $R^1$ is hydrogen methyl, chlorine or 2-thienyl;

$R^2$ is hydrogen or methlyl;

$R^3$ is hydrogen methyl, ethyl, isopropyl, isobutyl, methoxy or methylthio;

$R^4$ is hydrogen or methyl; and n is 0 and 2.

Still more preferably, the compound of the present invention has the structural formula (I) where R is methyl or isopropyl;

X is hydrogen or methyl;

$R^1$ is hydrogen, methyl or chlorine;

$R^2$ is hydrogen;

$R^3$ is hydrogen, methyl, ethyl, isobutyl or methylthio;

$R^4$ is hydrogen or methyl; and n is 0 or 2.

The compounds having the structural formula (I) have utility as insecticides. Thus, the compounds of this invention are utilized in insecticidal compositions. These insecticidal compositions comprise an insecticidally effective amount of a compound having the structural formula (I) where R, X, $R^1$, $R^2 R^3$, $R^4$ and n have their most general meanings and a carrier therefor.

More preferably, an insecticidal composition is provided which comprises an insecticidally effective amount of a compound having the structural formula (I) where R, X, $R^1$, $R^2 R^3$, $R^4$ and n have the meanings given above for the preferred embodiment of the compound of the present invention and a carrier therefor.

Still more preferably, the insecticidal composition of this invention comprises a compound having the structural formula (I) wherein R, X, $R^1$, $R^2$, $R_3$, $R^4$ and n have the meanings given for the most preferred group of compounds having structural formula (I) and a carrier therefor.

The insecticidal compositions of the present invention, as stated above, employ compounds having structural formula (I) in combination with a carrier. The carrier, within the contemplation of the composition of this invention, may be a finely divided or granular organic or inorganic inert material. Among the inert carriers within the contemplation of this invention are attapulgate clay, sand, vermiculite, corncobs, activated carbon and mineral silicates such as mica, talc, pyrophyllite and clays.

In another preferred embodiment of the composition of this invention the composition comprises a solution. That is, the active agent, a compound whose structural formula is (I), is dissolved in a suitable solvent which acts as the carrier. Among the solvents, acting as carrier, within the contemplation of this invention are acetone, methanol, isopropanol, t-butyl alcohol, cyclohexanol, n-butyl alcohol, cyclohexanone, toluene, xylene, dioxane, dimethylformamide, dimethylsulfoxide, ethylene dichloride and N-methylpyrrolidone.

In still another preferred embodiment of the composition of the present invention, the composition comprises a water emulsion carrier. The emulsion is prepared from a solution as described immediately above. To the solution is added a surface active agent. Surface active agents suitable for use in forming the emulsion of this invention are known to those skilled in the art. McCutcheon's Detergents and Emulsifiers, Allured Publishing Corp., Ridgewood, N.J. (1970); U.S. Pat. No. 2,514,916, Columns 2 to 4; and U.S. Pat. No. 2,547,734, Columns 3 and 4 provide detailed examples of such surface active agents. These agents may be anionic, non-ionic or cationic.

In yet still another preferred embodiment of the composition of this invention, the composition employs a dispersant as carrier. In this embodiment, the active insecticidal agent, a compound whose structural formula is (I), is mixed with a solvent of the type described above to form a solution which is added to one of the above-described surface active agents and water.

In still another embodiment of the composition of the instant invention, the active compound is premixed with an inert solid carrier which is added to a surface active agent and water to provide another form of dispersion within the contemplation of this invention.

The embodiment discussed immediately above, the disposal of the active agent on a solid inert carrier which is dispersed in a liquid to form a dispersion, may alternatively be employed in non-liquid form. That is, the composition of this invention may take the form of a dust, granules, a paste or a wettable powder. In these embodiments the active compound of this invention, the compound having the structural formula (I), is admixed with the inert carrier to form a solid composition. Thus, for example, in the embodiment wherein a powder is formed, the solid inert carrier is provided in powdered form. In many such cases, the inert carrier is a mineral silicate. The solid may be made wettable by the addition of a surface active agent, well known to those skilled in the art, and referred to in the above-recited references directed to surface active agents.

In another principal application of the composition of this invention an aerosol is prepared. To prepare an aerosol the active compound is dissolved in a first solvent. This first solvent is conventional in the sense that although the first solvent is volatile it is not highly volatile. This solution is then admixed with a highly volatile solvent, a so-called liquid aerosol carrier. The aerosol carrier is liquid only under elevated pressure. At ordinary temperatueres and at atmospheric pressure the aerosol carrier is a gas. In a subembodiment of this preferred embodiment the aerosol carrier may itself be active. For example, the carrier may be an insecticide, a herbicide, a bacteriacide or a plant growth regulant.

In another aspect of the present invention a method is provided for controlling insects wherein an insecticidally effective amount of a compound having the structural formula (I) where R, X, $R^1$, $R^2$, $R^3$, $R^4$, $R^5$, $R^6$ and n have the meanings given for the compound of the present invention is applied to the locus to be protected.

More preferably, the method for controlling insects comprising applying to the locus to be protected a insecticidally effective amount of a compound having the structural formula (I), entails using a compound within the meaning of structural formula (I) where R, X, $R^1$, $R^2$, $R^3$, $R^4$ and n have the meanings given for the preferred compounds of the present invention.

Still more preferably, the method for controlling insects includes the application of an insecticidally effective amount of a compound having the structural formula (I) where R, X, $R^1$, $R^2$, $R^3$, $R^4$ and n have the meanings given for the most prefered compounds of the present invention.

In a preferred embodiment of a method of the present invention, a method for controlling insects, the insects particularly amenable to control by the compound of the present invention, a compound having the structural formula (I), are corn rootworm, *Diabrotica undecimpunctata*, and rice planthopper, *Sogatodes oryzicola*. Of these, control of rice planthoppers by compounds of the present invention have been found to be quite effective at very low dosage rates.

The present invention also embodies a class of compounds having the structural formula

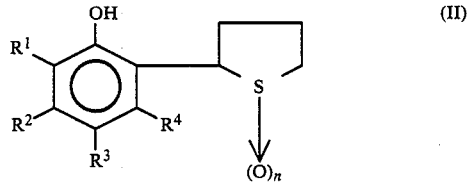

where $R^1$, $R^2$, $R^3$, and $R^4$ are the same or different and are hydrogen, halogen, $C_1-C_8$ alkyl, $C_1-C_2$ haloalkyl, $C_3-C_6$ cycloalkyl, $C_7-C_9$ aralkyl, phenyl, nitro, $C_1-C_6$ alkoxy, $C_1-C_6$ alkylthio, $C_1-C_6$ alkylsulfinyl, $C_1-C_6$ alkylsulfonyl, $C_7-C_9$ aralkoxy, phenoxy, phenylthio, phenylsulfinyl, phenylsulfonyl, tetrahydro-2-thienyl, dioxytetrahydro-2-thienyl, alkali metal carboxylate, $C_2-C_5$ alkoxycarbonyl, phenoxycarbonyl or $N(R^5)R^6$;

$R^5$ and $R^6$ are the same or different and are hydrogen or $C_1-C_6$ alkyl; and n is 0, 1 or 2 with the proviso that when $R^2$, $R^3$, and $R^4$ are each hydrogen and n is 0, $R^1$ cannot be methyl.

This class of new compound finds utility as an intermediate in the production of the insecticidally useful compounds defined by structural formula (I) as will be discussed below.

More preferably, the present invention encompasses a class of intermediate compounds having the structural formula (II) wherein $R^1$ is hydrogen, chlorine, phenyl, $C_1-C_6$ alkoxy, $C_2-C_5$ alkoxycarbonyl or tetrahydra-2-thienyl;

$R^2$ is hydrogen or methyl;

$R^3$ is hydrogen, methyl, ethyl, isopropyl, chlorine, methoxy, isopropyloxy, methylthio, methylsulfinyl, methysulfonyl, phenyl or nitro;

$R^4$ is hydrogen or methyl; and n is 0 or 2 with the proviso that if $R^1$, $R^3$, and $R^4$ are all hydrogen and n is 0, $R^2$ cannot be methyl.

Still more preferably, the present invention is directed to a compound having the structural formula (II) wherein $R^1$ is hydrogen or chlorine.

$R^2$ is hydrogen or methyl;

$R^3$ is methyl, chlorine, methylthio, methylsulfinyl, methylsulfonyl or nitro;

$R^4$ is hydrogen or methyl; and n is 0 or 2.

In still another aspect of the present invention a process for the production of compounds having the structural formula (I) where R, $R^1$, $R^2$, $R^3$, $R^4$, $R^5$, $R^6$, and n have the meanings given for compound (I) is provided. In this process a compound having a structural formula (II) wherein $R^1$, $R^2$, $R^3$, $R^4$, $R^5$, $R^6$, and n have the meanings given above is reacted with an alkyl isocyanate compound having the structural formula RNCO where R has the meanings given for the compound having the structural formula (I). The reaction is preferably catalyzed with a catalyst selected from the group consisting of trialkylamines and dialkyl tin oxalates.

The process preferably occurs under ambient conditions. That is, the reaction preferably takes place at ambient temperature and atmospheric pressure. The reaction, in addition, preferably occurs in solution. Thus, the compound having the structural formula (II) is dissolved in a solvent and then reacted with the alkyl isocyanate in the presence of the catalyst. Any organic solvent which does not react in this process can be utilized. In a preferred embodiment, the solvent is toluene. It is also preferred that the catalyst be triethylamine or dibutyl tin oxalate.

In yet another aspect of the present invention a process is provided for synthesizing the compound having the structural formula (II). In this reaction a phenol or substituted phenol having the structural formula

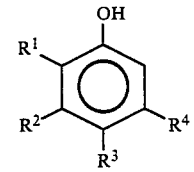

where where $R^{1'}$, $R^2$, Rqhu 3, and $R^4$ have the meanings given for the compound having the structural formula (II) is reacted with tetrahydrothiophene in the presence of N-chlorosuccinimide and triethylamine. This reaction preferably occurs at low temperature, between 0° C. and −70° C., more preferably between −45° C. and −65° C. The reaction is also preferably conducted in solution, with methylene chloride the preferred solvent.

The following examples are given to illustrate the scope of the present invention. Because these examples are given for illustrative purposes only, the invention embodied herein should not be limited to the actual examples provided.

EXAMPLE 1

Preparation of 2-(Tetrahydro-2-Thienyl)Phenol (Compound No. 1)

To a rapidly stirred mixtue of 64.0 g. (0.48 mol) of N-chlorosuccinimide dissolved in 2 liters of methylene chloride was added 46.5 g. (0.53 mol) of tetrahydrothiophene over a 10 minute period. This mixing occured at a temperature of between −5° and −10° C. After an additional 10 minutes, the temperature was lowered to −50° to −60° C. and 37.6 g. of phenol (0.40 mol) in 100 ml. methylene chloride was added over a 15 minute period. After an additional 30 minutes, 70 ml. (0.5 mol) of triethylamine was added at −50° to −60° C. and the reaction mixture was allowed to warm to room temperature. The reaction was concentrated in vacuo and the salts were dissolved in 2 liters of ether and extracted with 1.5 liters of water. The water was back-extracted with 1.5 liters of ether and the ethereal solutions were combined. The ether solution was successively washed with 1 liter of 3% hydrochloric acid, 1 liter of 3% aqueous sodium bicarbonate and two 500 ml. portions of water. The thus washed solution was thereafter dried over anhydrous sodium sulfate, filtered and concentrated.

Fractional distillation of the residue gave unreacted phenol, b.p. 55°-65° C. at 1.5 mm. Hg., followed by the recovery of 20 g. (46% yield based on the unreacted startup phenol) of the product, 2-(tetrahydro-2-thienyl)-phenol, b.p. 125°-135° at 0.1 mm. Hg.

EXAMPLE 2

Preparation of 2-(Tetrahydro-2-Thienyl)Phenol S,S-Dioxide (Compound No. 4)

To a stirred mixture of 20 g. of 30% hydrogen peroxide, 10 ml. water and a catalytic amount of sodium tungstate was added 3 g. of 2-(tetrahydro-2-thienyl)phenol, made in accordance with Example 1, maintaining the temperature of the reaction mixture at less than 50° C. upon addition of the phenol compound, a solid compound was obtained. The solid compound was filtered, washed with water and alcohol and dried in air.

The product, 2-(tetrahydro-2-thienyl)phenol S,S-dioxide, was obtained in a yield of 2 g. The product has a melting point of 180°–182° C. N.M.R. and IR confirmed the structure of the compound.

EXAMPLE 3

Preparation of 2-(tetrahydro-2-thienyl)phenol S-Oxide (Compound No. 15)

A solution of 5 g. of sodium metaperiodate in 80 ml water was added dropwise to a stirred solution of 4 g. of 2-(tetrahydro-2-thienyl)phenol, made in accordance with Example 1, in 40 ml of methanol at 0° C. and stirring was continued overnight at room temperature. Methanol was removed on a rotary evaporator and water added to the residue, which was then extracted with three 100 ml portions of methylene chloride. The combined methylene chloride extracts were dried with magnesium sulfate and then removed on a rotary evaporator, giving a solid product: amount 3 g. m.p. 150°–155° C.

EXAMPLES 4–41

Preparation of Compound Nos. 2, 3, 5 to 14 and 16 to 38

Following the procedure of Example 1, compounds having the structural formula (II) where n is 0 were synthesized. Similarly, compounds having the structural formula (II) where n is 2 or 1 were synthesized in accordance with the procedure of Example 2 and Example 3 respectively.

A summary of the compounds prepared, including Compounds No. 1, 4 and 15 prepared in accordance with Examples 1, 2 and 3 respectively, are summarized in Table 1. Table 1 defines the compound by its structue and included its boiling point if the compound, at atmospheric pressure, is a liquid at room temperature or its melting point if the compound is a solid at room temperature.

TABLE I

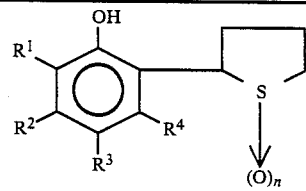

| Cpd. No. | $R^1$ | $R^2$ | $R^3$ | $R^4$ | n | B.P./M.P. °C. |
|---|---|---|---|---|---|---|
| 1 | H | H | H | H | 0 | 125–135/0.1 mm |
| 2 | $CH_3$ | H | H | H | 0 | 135–140/0.1 mm |
| 3 | $CH_3$ | H | H | H | 2 | 140–142 |
| 4 | H | H | H | H | 2 | 180–182 |
| 5 | H | H | $CH_3$ | H | 2 | 198–200 |
| 6 | H | $CH_3$ | H | $CH_3$ | 0 | 58–60 |
| 7 | H | H | $CH_3$ | H | 0 | 140–145/0.2 mm |
| 8 | H | H | $NO_2$ | H | 0 | 210–215/0.5 mm |
| 9 | H | H | Cl | H | 2 | 184–186 |
| 10 | H | H | Cl | H | 0 | 155–160/0.2 mm |
| 11 | Cl | H | Cl | H | 0 | 55–60 |
| 12 | Cl | H | Cl | H | 2 | 203–250 |
| 13 | H | H | $SCH_3$ | H | 0 | 180–185/0.5 mm |
| 14 | H | H | $SO_2CH_3$ | H | 2 | 225–230 |
| 15 | H | H | H | H | 1 | 150–155 |
| 16 | H | H | $CH_3$ | H | 1 | 125–130 |
| 17 | H | $CH_3$ | H | H | 0 | 145–150/0.3 mm |
| 18 | H | H | H | $CH_3$ | 0 | 140–142/0.3 mm |
| 19 | H | H | $C_2H_5$ | H | 0 | 155–160/0.5 mm |
| 20 | H | H | $C_2H_5$ | H | 2 | 169–170 |
| 21 | H | H | $CH(CH_3)_2$ | H | 0 | 175–180/0.5 mm |
| 22 | H | H | $CH(CH_3)_2$ | H | 1 | oil |
| 23 | H | H | $C(CH_3)_3$ | H | 0 | 165–170/0.5 mm |
| 24 | H | H | $C(CH_3)_3$ | H | 2 | 87–89 |
| 25 | H | H | $CHCH_3(C_2H_5)$ | H | 1 | 170–180/0.5 mm |
| 26 | $OCH(CH_3)_2$ | H | H | H | 0 | 160–165/0.5 mm |
| 27 | $OCH(CH_3)_2$ | H | H | H | 2 | 58–60 |
| 28 | $OCH(CH_3)_2$ | H | H | H | 1 | oil |
| 29 | $C_6H_5$ | H | H | H | 1 | 57–58 |
| 30 | $C_6H_5$ | H | H | H | 2 | 200 |
| 31 | $COOCH_3$ | H | H | H | 0 | oil |
| 32 | H | H | $CH(CH_3)_2$ | H | 2 | 147–148 |
| 33 | H | H | $C_2H_5$ | H | 1 | oil |
| 34 | H | H | $OCH_3$ | H | 0 | 145–150/0.5 mm |
| 35 | tetrahydro-2-thienyl | H | H | H | 0 | 62–65 |
| 36 | tetrahydro-2-thienyl | H | $OCH_3$ | H | 0 | 210–215/0.5 mm |
| 37 | dioxytetra- | H | $SO_2CH_3$ | H | 2 | 235–238 |

TABLE I-continued

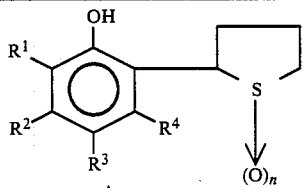

| Cpd. No. | R¹ | R² | R³ | R⁴ | n | B.P./M.P. °C. |
|---|---|---|---|---|---|---|
| 38 | hydro-2-thienyl tetrahydro-2-thienyl | H | SCH₃ | H | 0 | 210–215/0.5 mm |

EXAMPLE 42

Preparation of 2-(Tetrahydro-2-Thienyl)Phenol Monomethyl Carbamate (Compound No. 39)

To 3.8 g. of 2-(tetrahydro-2-thienyl)phenol, dissolved in 50 ml. of toluene, was added 1.8 g. of methyl isocyanate and 0.5 ml. triethylamine. The mixture was stirred at room temperature overnight and then washed with water. The toluene layer of the resultant two-phase product was dried over sodium sulfate and the solvent removed.

The product, 2-(tetrahydro-2-thienyl)phenol monomethyl carbamate, was obtained as a solid having a melting point of 98°–100° C.

EXAMPLE 43

Preparation of 2-(Tetrahydro-2-Thienyl)Phenol S,S-Dioxide Monomethyl Carbamate (Compound No. 48)

In substantial accordance with the procedure of Example 39, the monomethyl carbamate of 2-(tetrahydro-2-thienyl) S,S-dioxide was prepared. The procedure of Example 39 was amended to the extent that, instead of triethylamine, dibutyl tin oxalate was employed as the catalyst.

The S,S-dioxide compound was also synthesized from 2-(tetrahydro-2-thienyl)phenol monomethyl carbamate in accordance with the procedure of Example 2 employing 30% hydrogen peroxide, water and sodium tungstate as catalyst.

The solid product of this synthesis, 2-(tetrahydro-2-thienyl)phenol S,S-dioxide monomethyl carbamate, was characterized by a melting point of 120°–122° C.

EXAMPLE 44

Preparation of A-methyl-2-(tetrahydro-2-thienyl)phenol Dimethyl Carbamate (Compound No. 67)

4 grams of 4-methyl-2-(tetrahydro-2thienyl)phenol was dissolved in 50 ml toluene. To this solution was added 1 gram of sodium hydride (60%) which was washed twice with small amounts of toluene. The mixture was stirred at room temperature for 1 hour and then 2 grams of dimethylarbamoyl chloride was added to it. This mixture was refluxed for 8 hours, cooled and the toluene solution was washed twice with water. It was dried with anhydrous sodium sulfate, filtered and toluene was removed. A solid was obtained. Amount: 3 gram, m.p. 82°–85°.

EXAMPLE 45–77

Preparation of Compound Nos. 40–47 and 49–66 and 68–72

Following the procedures of Examples 42, 43 and 44 Compound Nos. 40–47, 49–66 and 68–72 were prepared.

A summary of these compounds, which were mostly solids at room temperature, are included in Table 2. These Compound Nos. 39–72 were characterized by their melting points, unless they are viscous liquids or wax.

TABLE II

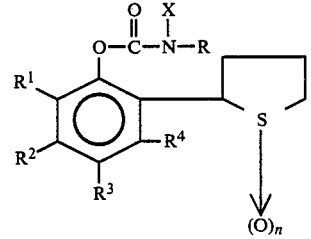

| Cpd. No. | X | R | R¹ | R² | R³ | R⁴ | n | M.P., °C. |
|---|---|---|---|---|---|---|---|---|
| 39 | H | CH₃ | H | H | H | H | 0 | 98–100 |
| 40 | H | CH₃ | CH₃ | CH₃ | H | H | 0 | 109–111 |
| 41 | H | CH₃ | 2-thienyl | " | H | H | 0 | 182–183 |
| 42 | H | CH₃ | H | " | CH₃ | H | 0 | 115–117 |
| 43 | H | CH₃ | H | CH₃ | H | CH₃ | 0 | 74–75 |
| 44 | H | CH(CH₃)₂ | H | H | H | H | 0 | 103–105 |
| 45 | H | C₆H₁₁ | H | H | H | H | 0 | 125–127 |

TABLE II-continued

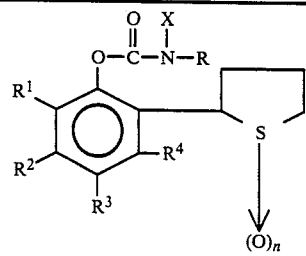

| Cpd. No. | X | R | R¹ | R² | R³ | R⁴ | n | M.P., °C |
|---|---|---|---|---|---|---|---|---|
| 46 | H | $CH_3$ | H | H | $NO_2$ | H | 0 | 154-155 |
| 47 | H | $CH_3$ | Cl | H | Cl | H | 0 | 160-162 |
| 48 | H | $CH_3$ | H | H | Cl | H | 2 | 120-122 |
| 49 | H | $CH_3$ | H | H | Cl | H | 0 | 135-136 |
| 50 | H | $CH_3$ | H | H | $SCH_3$ | H | 0 | 115-117 |
| 51 | H | $CH_3$ | H | H | $CH_3$ | H | 2 | 109-110 |
| 52 | H | $CH_3$ | H | H | $C(CH_3)_3$ | H | 0 | wax |
| 53 | H | $CH_3$ | H | H | $C_2H_5$ | H | 2 | oil |
| 54 | H | $CH_3$ | H | H | " | H | 0 | 107-108 |
| 55 | H | $CH_3$ | H | H | $i-C_3H_7$ | H | 0 | oil |
| 56 | H | $CH_3$ | H | H | H | H | 1 | 125-127 |
| 57 | H | $CH_3$ | H | H | $CH_3$ | H | 1 | 128-130 |
| 58 | H | $CH_3$ | H | $CH_3$ | H | H | 0 | 118-120 |
| 59 | H | $CH_3$ | H | H | H | $CH_3$ | 0 | 134-137 |
| 60 | H | $CH_3$ | H | H | H | $CH_3$ | 2 | 130-132 |
| 61 | H | $CH_3$ | H | H | $C_2H_5$ | H | 1 | 96-98 |
| 62 | H | $CH_3$ | H | H | $CH(CH_3)_2$ | H | 2 | 116-118 |
| 63 | H | $CH_3$ | $OCH(CH_3)_2$ | H | " | H | 0 | 100-101 |
| 64 | H | $CH_3$ | " | H | " | H | 1 | 100-102 |
| 65 | H | $CH_3$ | $COOCH_3$ | H | H | H | 0 | oil |
| 66 | H | $CH_3$ | H | H | $OCH_3$ | H | 0 | 110-112 |
| 67 | $CH_3$ | $CH_3$ | H | H | $CH_3$ | H | 0 | 82-85 |
| 68 | $CH_3$ | $CH_3$ | H | H | " | H | 1 | oil |
| 69 | $CH_3$ | $CH_3$ | H | H | " | H | 2 | 120-122 |
| 70 | $CH_3$ | $CH_3$ | H | H | H | H | 2 | 115-118 |
| 71 | $CH_3$ | $CH_3$ | H | H | $OCH_3$ | H | 0 | oil |
| 72 | $CH_3$ | $CH_3$ | H | H | $SCH_3$ | H | 0 | oil |

EXAMPLE 78

Preparation of Insecticidal Compositions

Each of Compound Nos. 39-72 were formed into compositions. This was accomplished by dissolving 0.3 g. of each of the compounds in 10 ml. of acetone to which was added four drops of a suitable wetting agent. Each of these solutions was diluted with a 100 ml. of water forming a 3,000 ppm suspension. Additional compositions having a concentration of 1,000 ppm were prepared by further diluting the 3,000 ppm composition with water. In addition to the compositions having 3,000 and 1,000 ppm concentration, compositions having a concentration of 500 ppm were prepared by diluting the 1,000 ppm concentration compositions with an equal amount of water.

EXAMPLES 79-112

Control of Rice Planthoppers

Compositions of Compound Nos. 39-72, made in accordance with Example 78, having a concentration of 1,000 ppm, were sprayed onto two rice seedling plants with a spray atomizer. One day following this treatment ten adult rice planthoppers, *Sogatodes oryzicola*, were placed on the two seedling plants.

Controls were also provided by duplicating this treatment except that the active compounds (Compounds Nos. 39-72) were not applied. The controls, however, included the placement on the control rice seedling plants of ten adult rice planthoppers.

The surviving planthoppers were counted after five days to determine percent control in accordance with testing procedures well established in the art.

The results of these tests are summarized below in Table 3. Table 3 summarizes percent control for each of Compound Nos. 39-72 within the contemplation of structural formula (I).

TABLE III

| Control of Rice Planthoppers | |
|---|---|
| Compound No. | % Control at 1000 ppm |
| 39 | 100 |
| 40 | 0 |
| 41 | 0 |
| 42 | 50 |
| 43 | 50 |
| 44 | 95 |
| 45 | 0 |
| 46 | 0 |
| 47 | 0 |
| 48 | 75 |
| 49 | 80 |
| 50 | 100 |
| 51 | 100 |
| 52 | 0 |
| 53 | 0 |
| 54 | 100 |
| 55 | — |
| 56 | 100 |
| 57 | 100 |
| 58 | 90 |
| 59 | 100 |
| 60 | 100 |
| 61 | 100 |
| 62 | 0 |

TABLE III-continued

Control of Rice Planthoppers

| Compound No. | % Control at 1000 ppm |
| --- | --- |
| 63 | 30 |
| 64 | 0 |
| 65 | 0 |
| 66 | 100 |
| 67 | 100 |
| 68 | 50 |
| 69 | 95 |
| 70 | 100 |
| 71 | 100 |
| 72 | 100 |

EXAMPLES 112-121

Systemic Control of Rice Planthoppers

To determine the systemic insecticidally effect of the carbamate compounds of the present invention, 200 ppm concentration compositions of ten compounds within the contemplation of the present inventions were prepared. These suspensions were prepared in accordance with the procedure of Example 78 wherein the decreased concentration was prepared by further water dilution.

Thirty ml. of the 200 ppm suspensions were syringe injected under the root system of two rice seedling plants in a pot containing 570 g. of potting soil. The resulting active compound concentration in the soil was 10 ppm. One day after this treatment 10 adult rice planthoppers, *Sogatodes oryzicola*, were placed on the plant and confined thereon using a plaster cylinder. Similarly, controls were prepared wherein the procedure above was repeated without the syringe injection of the active compounds.

Five days after injection of the rice planthoppers, the pots were inspected to determine the number of surviving planthoppers. After comparing the controls with the active insecticidal compositions the percent control was reported in accordance with reporting procedures well established in the art. The results of this test are summarized in Table 4 below.

TABLE IV

Systematic Control of Rice Planthoppers

| Compound No. | % Control at 10 ppm |
| --- | --- |
| 39 | 100 |
| 42 | 100 |
| 51 | 100 |
| 56 | 100 |
| 57 | 100 |
| 58 | 63 |
| 59 | 95 |
| 60 | 100 |
| 69 | 100 |
| 70 | 100 |

EXAMPLES 121-154

Control of Southern Corn Rootworm

Five ml. of the 500 ppm insecticidal compositions made in accordance with Example 78 were pipetted onto paper towels and inserted into plastic bags. Two corn seedlins were also soaked in these 500 ppm. suspension compositions and also inserted into the same plastic bag. At the same time inert compositions were prepared which did not include the active compounds. These inert compositions were similarly disposed on the paper towels and corn seedlings. All the bags were held for 18 hours and then loaded with five corn rootworm, *Diabrotica undecimpuntata*, larvae. After 6 days, the number of live larvae were noted and the percent control calculated.

The results of this test, which utilized Compounds Nos. 39-72, are summarized in Table 5 below.

TABLE V

Control of Corn Rootworm

| Compound No. | % Control at 500 ppm |
| --- | --- |
| 39 | 100 |
| 40 | 100 |
| 41 | 50 |
| 42 | 50 |
| 43 | 50 |
| 44 | 78 |
| 45 | 60 |
| 46 | 40 |
| 47 | 100 |
| 48 | 56 |
| 49 | 100 |
| 50 | 75 |
| 51 | 100 |
| 52 | 100 |
| 53 | 80 |
| 54 | 100 |
| 55 | 100 |
| 56 | 100 |
| 57 | 58 |
| 58 | 100 |
| 59 | 100 |
| 60 | 100 |
| 61 | 100 |
| 62 | 58 |
| 63 | 100 |
| 64 | 100 |
| 65 | 80 |
| 66 | 100 |
| 67 | 100 |
| 68 | 0 |
| 69 | 20 |
| 70 | 100 |
| 71 | 20 |
| 72 | 100 |

The above mentioned embodiments and examples illustrate the scope and spirit of the instant invention. These embodiments and examples will make apparent, to those skilled in the art, other embodiments and examples. These other embodiments and examples are within the contemplation of the present invention. Therefore, the instant invention should be limited only by the appended claims.

What is claimed is:

1. A compound having the structural formula

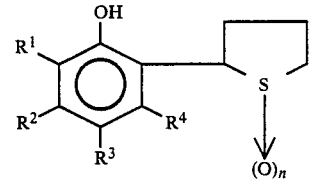

where $R^1$, $R^2$, $R^3$ and $R^4$ are the same or different and are hydrogen, halogen, $C_1$-$C_8$ alkyl, $C_1$-$C_2$ haloalkyl, $C_3$-$C_6$ cycloalkyl, $C_7$-$C_9$ aralkyl, phenyl, nitro, $C_1$-$C_6$ alkoxy, $C_1$-$C_6$ alkylthio, $C_1$-$C_6$ alkylsulfinyl, $C_1$-$C_6$ alkylsulfonyl, $C_7$-$C_9$ aralkoxy, phenoxy, phenylthio, phenylsulfinyl, phenylsulfonyl, tetrahydro-2-thienyl, dioxytetrahydro-2-thienyl, alkali metal carboxylate, $C_2$-$C_5$ alkoxycarbonyl, phenoxycarbonyl or $N(R^5)R^6$;

$R^5$ and $R^6$ are the same or different and are hydrogen of $C_1$–$C_2$ alkyl; and n is 0, 1 or 2; with the proviso that when $R^1$, $R^3$ and $R^4$ are each hydrogen and n is 0, $R^2$ cannot be methyl.

2. A compound in accordance with claim 1 wherein $R^1$ is hydrogen, chlorine, phenyl, $C_1$–$C_6$ alkoxy, $C_2$–$C_5$ alkoxycarbonyl or tetrahydro-2-thienyl;

$R^2$ is hydrogen or methyl;

$R^3$ is hydrogen, methyl, ethyl, isopropyl, chlorine, methoxy, isopropyloxy, methylthio, methylsulfinyl, methylsulfonyl, phenyl or nitro;

$R^4$ is hydrogen or methyl; and n is 0 or 2 with the proviso that when $R^1$, $R^3$ and $R^4$ are each hydrogen and n is 0, $R^2$ cannot be methyl.

3. A compound in accordance with claim 2 wherein $R^1$ is hydrogen or chlorine; and $R^3$ is methyl, chlorine, methylthio, methylsulfinyl, methylsulfonyl or nitro.

* * * * *